United States Patent
Fox et al.

(10) Patent No.: US 11,458,326 B2
(45) Date of Patent: Oct. 4, 2022

(54) SYSTEM, APPARATUS AND METHODS FOR IMAGE-GUIDED, ROBOTICALLY DELIVERED TRANSCRANIAL MAGNETIC STIMULATION (IRTMS) TREATMENT

(71) Applicants: Peter T. Fox, San Antonio, TX (US); Jack L. Lancaster, San Antonio, TX (US); Felipe Santiago Salinas, San Antonio, TX (US)

(72) Inventors: Peter T. Fox, San Antonio, TX (US); Jack L. Lancaster, San Antonio, TX (US); Felipe Santiago Salinas, San Antonio, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 436 days.

(21) Appl. No.: 16/600,889

(22) Filed: Oct. 14, 2019

(65) Prior Publication Data
US 2020/0114161 A1    Apr. 16, 2020

Related U.S. Application Data

(60) Provisional application No. 62/745,626, filed on Oct. 15, 2018.

(51) Int. Cl.
*A61N 2/00* (2006.01)
*A61B 5/055* (2006.01)
*A61B 5/00* (2006.01)
*A61N 2/02* (2006.01)

(52) U.S. Cl.
CPC ............ *A61N 2/006* (2013.01); *A61B 5/0042* (2013.01); *A61B 5/055* (2013.01); *A61B 5/7267* (2013.01); *A61N 2/02* (2013.01)

(58) Field of Classification Search
CPC ..... A61B 5/7267; A61B 5/4836; A61B 5/055; A61B 5/0042; A61B 5/0006; A61B 5/369; A61B 5/165; A61B 5/24; A61B 5/486; A61N 2/006; A61N 2/02; A61N 1/36025; A61N 1/36082; A61M 2230/10; A61M 2021/0055; A61M 21/02; A61M 2230/005; A61M 21/00; G01R 33/4806; G01R 33/4808; G06F 3/015; G16H 20/70;
(Continued)

(56) References Cited

U.S. PATENT DOCUMENTS

| | | |
|---|---|---|
| 7,087,008 B2 | 8/2006 | Fox et al. |
| 7,658,704 B2 | 2/2010 | Fox et al. |
| 9,265,965 B2 | 2/2016 | Fox et al. |

(Continued)

OTHER PUBLICATIONS

Peter T. Fox, Declaration of Peter T. Fox with Exhibits A & B, pp. 1-25, May 19, 2022.

*Primary Examiner* — Christine H Matthews
*Assistant Examiner* — Joshua Daryl D Lannu
(74) *Attorney, Agent, or Firm* — Trop, Pruner & Hu, P.C.

(57) ABSTRACT

Transcranial magnetic stimulation may be delivered to a subject based on a treatment plan. This treatment plan is generated using connectivity-image guidance to identify one or more optimal locations to stimulate based on network properties. In turn, a cortical column cosine principle may be applied to identify one or more particular subject locations at which to deliver TMS to the subject to the optimal locations.

19 Claims, 11 Drawing Sheets

(58) Field of Classification Search
CPC ........ G16H 50/20; G16H 50/70; G16H 70/60; G06K 9/00536; G06N 3/02
See application file for complete search history.

(56) References Cited

U.S. PATENT DOCUMENTS

| | | | |
|---|---|---|---|
| 2003/0050527 A1* | 3/2003 | Fox | A61N 2/006 600/13 |
| 2009/0227830 A1* | 9/2009 | Pillutla | A61N 2/02 600/13 |
| 2015/0119689 A1* | 4/2015 | Pascual-Leone | A61N 2/006 600/407 |

* cited by examiner

PCL-5 Raw Scores

| | | In Hospital | | | Post Discharge | |
|---|---|---|---|---|---|---|
| Active | Baseline | Rx 1 Wk | Rx 2 Wk | Rx 3 Wk | FU 1 Mo | FU 3 Mo |
| Mean | 59.57 | 43.49 | 38.41 | 33.29 | 28.35 | 34.47 |
| SD | 9.94 | 16.47 | 19.16 | 19.86 | 14.57 | 19.06 |
| n | 60 | 55 | 51 | 51 | 26 | 15 |
| Sham | | | | | | |
| Mean | 60.07 | 48.62 | 41.57 | 38.8 | 40.22 | 46.64 |
| SD | 11.74 | 16.19 | 18.14 | 19.36 | 22.81 | 22.61 |
| n | 61 | 58 | 54 | 59 | 27 | 14 |

SYSTEM, APPARATUS AND METHODS FOR IMAGE-GUIDED, ROBOTICALLY DELIVERED TRANSCRANIAL MAGNETIC STIMULATION (IRTMS) TREATMENT

This application claims priority to U.S. Provisional Patent Application No. 62/745,626, filed on Oct. 15, 2018, in the names of Peter T. Fox, Jack L. Lancaster, and Felipe Santiago Salinas, entitled SYSTEM, APPARATUS AND METHODS FOR IMAGE-GUIDED, ROBOTICALLY DELIVERED TRANSCRANIAL MAGNETIC STIMULATION (irTMS) TREATMENT, the disclosure of which is hereby incorporated by reference.

BACKGROUND

In transcranial magnetic stimulation (TMS), magnetic fields pass readily through biological tissues, including bone. Rapidly changing magnetic fields induce electrical currents that, in turn, depolarize neurons. TMS stimulation of the brain was first achieved by Barker et al. (1985), stimulating the primary motor cortex. In the 1950's, Donald Hebb described the principle of Hebbian learning, which states that repetitive firing of a neural system will be neuromodulatory. Current formulations of this principle are long-term potentiation (LTP) and long-term depression (LTD), which have been firmly established in a wide range of species, including humans. Based on the Hebbian neuromodulatory principle, repetitive transcranial magnetic stimulation (rTMS) has been tested in hundreds of trials in scores of disorders, including major depressive disorder (MDD) and post-traumatic stress disorder (PTSD).

Repetitive transcranial magnetic stimulation is a non-invasive neuromodulatory treatment modality that is approved by regulatory bodies in the United States (FDA), Canada, Europe and Australia for MDD. FDA approval for rTMS treatment of MDD was based on a double-blind, placebo-controlled (sham TMS), multi-center clinical trial. In that trial, the neuroanatomical location targeted was the left dorsolateral prefrontal cortex (DLPFC), based on functional neuroimaging evidence that it serves as a hub in a multi-node network dysregulated in MDD. A similar approach was adopted in previous rTMS treatment trials of PTSD when targeting the right DLPFC. However, these rTMS targeting methods are neurophysiologically, neuroanatomically and technically unsophisticated. Specifically, (left or right) DLPFC was located by reference to the hand region of primary motor cortex (M1hand), rather than being based on per-subject anatomy or connectivity. The orientation in which the coil was positioned (with the E-field vector pointed toward the patient's nose) was (grossly) optimized for M1hand, but did not account for differences in gyral anatomy between locations (DLPFC versus M1hand) or between subjects; these studies were also not image-guided. This is the standard-of-care for TMS treatment of MDD.

DETAILED DESCRIPTION

In various embodiments, connectivity-image guidance (CIG) treatment planning may be used for directing TMS delivery. More specifically, embodiments may extend application of a cortical column cosine (C3) principle for directing TMS by combining it with a CIG principle. The C3 principle describes how to effectively stimulate any cortical location, based on local anatomy. The CIG principle identifies optimal locations to stimulate based on their network properties, that is, by their functional connectivity to other brain areas. Network participation is determined in a two-stage manner. First, meta-analytic connectivity-based parcellation (CBP) is used to make a population connectivity model for the network of interest. Second, resting-state BOLD fMRI is used to compute a per-subject match to the population model. This per-subject connectivity map is then used to inform the C3 modeling of where to target.

More specifically, in a particular embodiment described herein, connectivity-based parcellation (CBP) was applied to BrainMap task-activation data to identify sub-zones within dorsolateral prefrontal cortex (DLPFC) based on their remote co-activation patterns. In this instance, DLPFC includes two major sub-zones, a postero-lateral sub-zone and an antero-medial sub-zone. The antero-medial sub-zone projected to sub-genual cingulate, a region known to be implicated in depression, post-traumatic stress disorder and other psychiatric disorders. Based on this, antero-medial DLPFC may be selected as the "up-stream target" to be stimulated to produce a predicted modulatory effect in sub-genual cingulate.

The precise location to be stimulated can be determined by: 1) computing "region-seeded" (region to whole brain) connectivity of resting-state functional MRI (fMRI) for the sub-genual cingulate, on a per-patient basis; 2) identifying within DLPFC, the projection zones (from sub-genual cingulate), thereby; 3) applying the C3 principle using overlaid structural MRI and rs-fMRI, to optimize the DLPFC "up-stream target" to modulate the sub-genual cingulate "down-stream target"; and 4) delivering the TMS treatment plan robotically. In turn, follow-up brain imaging can be performed after some number of, e.g., consecutive daily irTMS treatments, to confirm efficacy of targeting.

Figure 1:
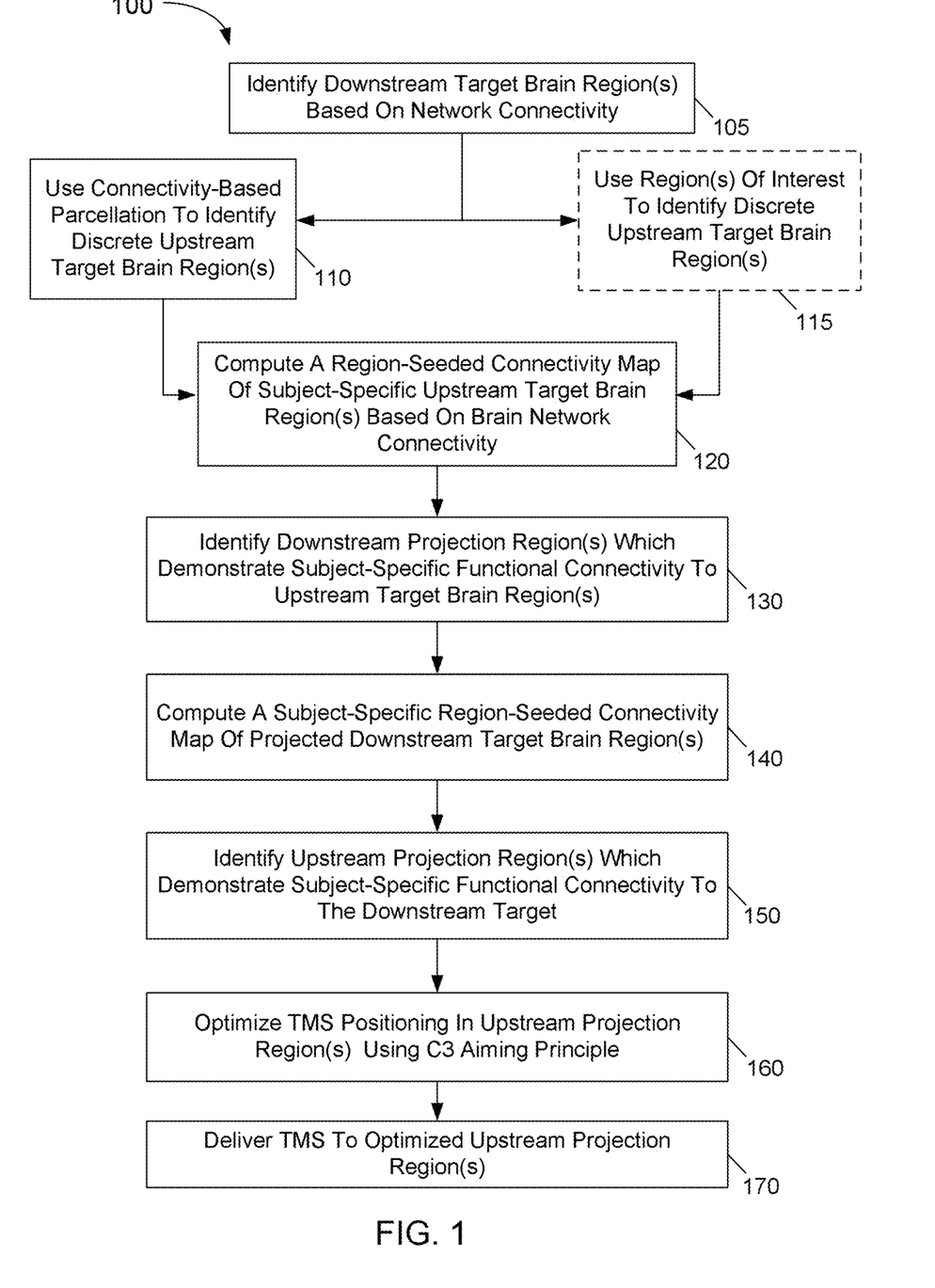
FIG. 1 is a flow diagram of a method in accordance with an embodiment of the present invention.

Referring now to FIG. 1, shown is a flow diagram of a method in accordance with an embodiment of the present invention. More specifically, method 100 of FIG. 1 is a method for performing treatment planning and delivery of TMS to a subject, e.g., a human patient. As such, method 100 may be performed by hardware circuitry, firmware, software and/or combinations thereof. In particular embodiments herein, method 100 may be performed using software executed on one or more computing systems to generate a treatment plan that is then executed by a robotic system to deliver TMS to the subject. In method 100, first a group or meta-analytic level analysis is performed to identify discrete upstream target brain regions. Thereafter, based on subject-specific mapping of brain locations using imaging systems and so forth, at least one appropriate upstream projection region of the subject may be identified. Thereafter, optimized TMS positioning can be determined to thus generate a treatment plan, which may be implemented within a non-transitory storage medium. In turn, information stored in this storage medium may be communicated to a robotic TMS system to deliver the TMS to the subject.

More specifically as illustrated in FIG. 1, method 100 begins by first performing operations that are provided at a group (or meta-analytic) level by identifying one or more downstream target brain regions based on network connectivity (block 105). In the particular embodiment described herein, a particular downstream target brain region is the sub-genual cingulate gyrus. In turn, control passes to either of blocks 110 or 115 to identify one or more discrete upstream target brain regions. In the particular embodiment herein, this upstream region is the anterior DLPFC. With reference to FIG. 1, depending upon implementation this identification may occur using connectivity-based parcellation (at block 110) or using regions of interest (at block 115).

In either event, control passes to block 120 et seq. where operations are performed at a subject level, i.e., for a particular patient. As seen at block 120, a region-seeded connectivity map may be computed for the subject. More specifically, this region-seeded connectivity map is of a subject-specific upstream target brain region (or regions) based on brain network connectivity. Next at block 130 one or more downstream projection regions can be identified. More specifically, these regions demonstrate subject-specific functional connectivity to the upstream target brain region(s). Thereafter at block 140, a subject-specific region-seeded connectivity map may be computed. More specifically, this map is of the one or more projected downstream target brain regions. Next at block 150, one or more upstream projection regions can be identified. More specifically, these upstream regions are those that demonstrate subject-specific functional connectivity to the downstream region, which may be based at least in part on the imaging data for the subject.

Still with reference to FIG. 1, thereafter at block 160 TMS positioning may be optimized for this subject in the upstream projection region using the C3 aiming principle. In an embodiment, the C3 aiming principle and its use for optimizing TMS positioning may be performed in accordance with the techniques disclosed in one or more of U.S. Pat. Nos. 7,087,008, 7,658,704 and 9,265,965, the disclosures of which are hereby incorporated by reference. As such, this optimized TMS positioning results in generation of a treatment plan to control robotic positioning and delivery of TMS.

This treatment plan may be implemented in a non-transitory storage medium. Instructions and/or data of this medium may then be communicated to a robotic system, which thus delivers the TMS to the optimized upstream projection region or regions via a TMS coil of the robotic system (block 170). Understand while shown at this high level, many variations and alternatives are possible.

In some cases, a treatment plan for delivering TMS to a patient may be generated using a machine learning application, in which image data of a subject (patient) is received by the machine learning application and is compared to a dataset that includes images and corresponding treatment plans. Based upon a degree of similarity to one or more of the entries in this dataset, a treatment plan may be automatically determined.

Figure 2:
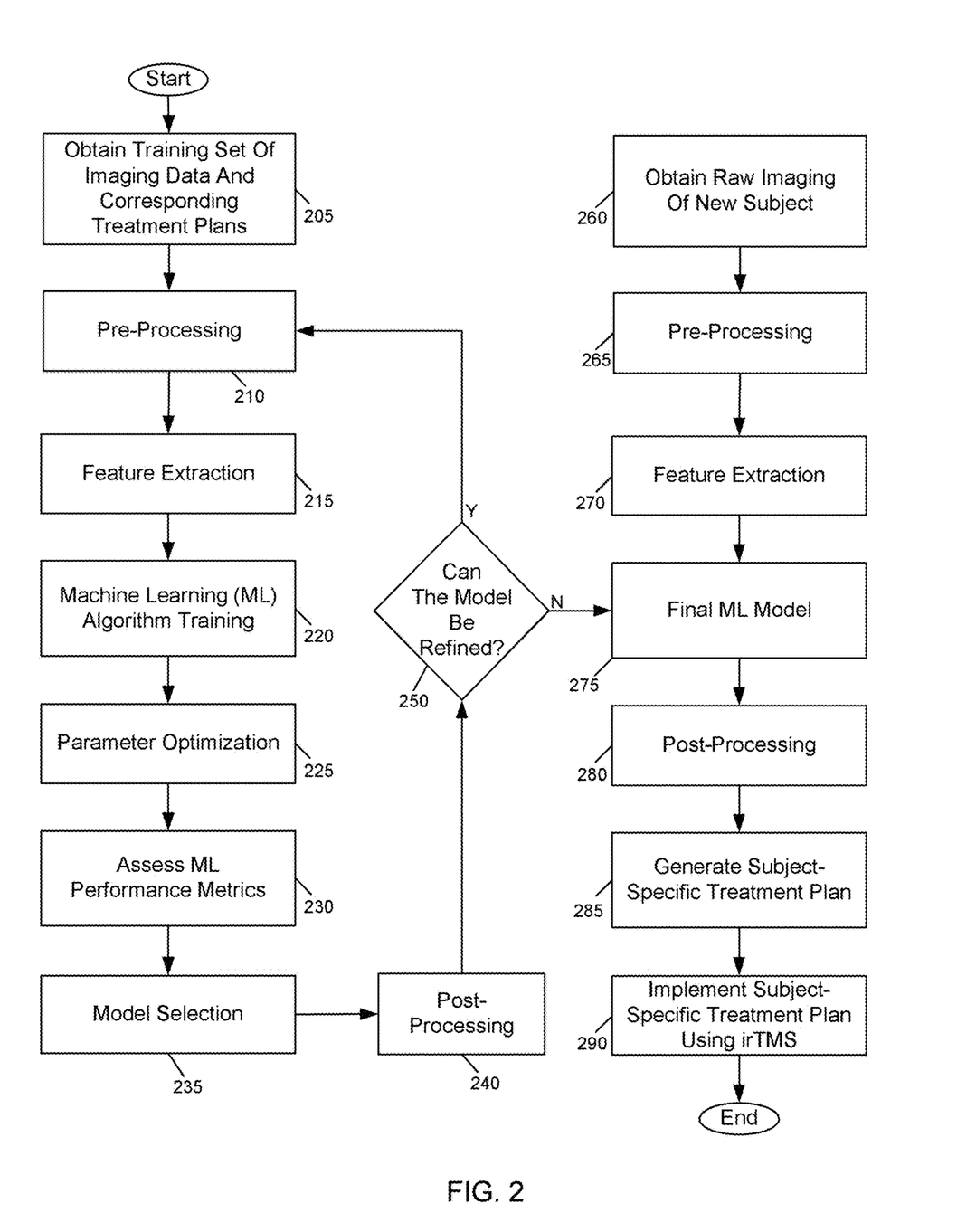
FIG. 2 is a flow diagram of a method in accordance with an embodiment.

Referring now to FIG. 2, shown is a flow diagram of a method in accordance with an embodiment. More specifically, FIG. 2 is a method for generating a model for automatically determining a treatment plan for TMS delivery by analysis of a training set using a supervised or unsupervised classifier. And then actual image data of a patient (subject) may be fed to the model to automatically generate a treatment plan. As such, method 200 may be performed by hardware circuitry, software, firmware and/or combinations thereof. For example, one or more computing systems may perform method 200.

As illustrated, method 200 begins by obtaining a training set of imaging data and corresponding treatment plans (block 205). Such training set may be obtained based on clinical trials or other uses of TMS delivery to treat a particular disease, disorder, condition or for other therapeutic benefit. At block 210, pre-processing of the received information may be performed. As examples, this pre-processing may include: signal equilibration; motion correction; slice timing correction; brain extraction; nuisance signal regression; spatial smoothing; and temporal filtering. Thereafter, control passes to block 215 where a feature extraction process may be performed to extract features from the data. As examples, the extracted features may include seed and/or network-based functional connectivity maps of a behavior, disease or disorder.

Still with reference to FIG. 2, next at block 220 training of a machine learning algorithm may be performed, followed by parameter optimization at block 225. Then at block 230, machine learning performance metrics may be assessed (e.g., classification accuracy, F1 score (precision v. recall), area under curve (sensitivity v. specificity), logarithmic loss, confusion matrices, mean absolute error, and mean squared error). Next at block 235, a model selection process is performed. More specifically, this model is for determining a treatment plan. Finally, at block 240, post-processing of the selected model may occur. This post-processing may include knowledge filtering, model re-evaluation, and knowledge integration. Then it may be determined at diamond 250 whether the model can be refined. If so, control passes back to block 210. Otherwise, a final machine learning model is formed at block 275.

At this point in method 200, a machine learning model has thus been generated and can be used to develop treatment plans for various subjects seeking TMS delivery for a common disease, disorder, condition or for other therapeutic benefit. Thus still with reference to FIG. 2, at block 260 the model may receive raw imaging data of a new subject. This imaging data may include, at least, fMRI data for the subject. Next, this raw imaging data may be pre-processed (block 265). For example, the data may be pre-processed in a manner similar to that discussed above in block 210. Then at block 270 features may be extracted from the pre-processed data.

This data may be applied to the final machine learning model, after which post-processing is performed (block 280). Next, control passes to block 285 where a subject-specific treatment plan may be generated in the model using this subject's processed imaging data. Note that this treatment plan may include various parameters for TMS delivery, including delivery rate, time duration, intensity levels and so forth, as well as appropriate positioning of the TMS coil with respect to the subject's body. Then at block 290, the subject may be treated according to the generated treatment plan. More specifically image-guided robotically-delivered TMS delivery may be performed. Although shown at this high level in the embodiment of FIG. 2, many variations and alternatives are possible. That is, the "downstream aiming" method is general and applicable to many disorders, and not just MDD or PTSD. Thus other embodiments may be used to compute "downstream aiming" targeting for other behaviors, diseases, disorders and other brain regions.

Further implementation details of a representative trial and its analyses are described below.

Figure 3:
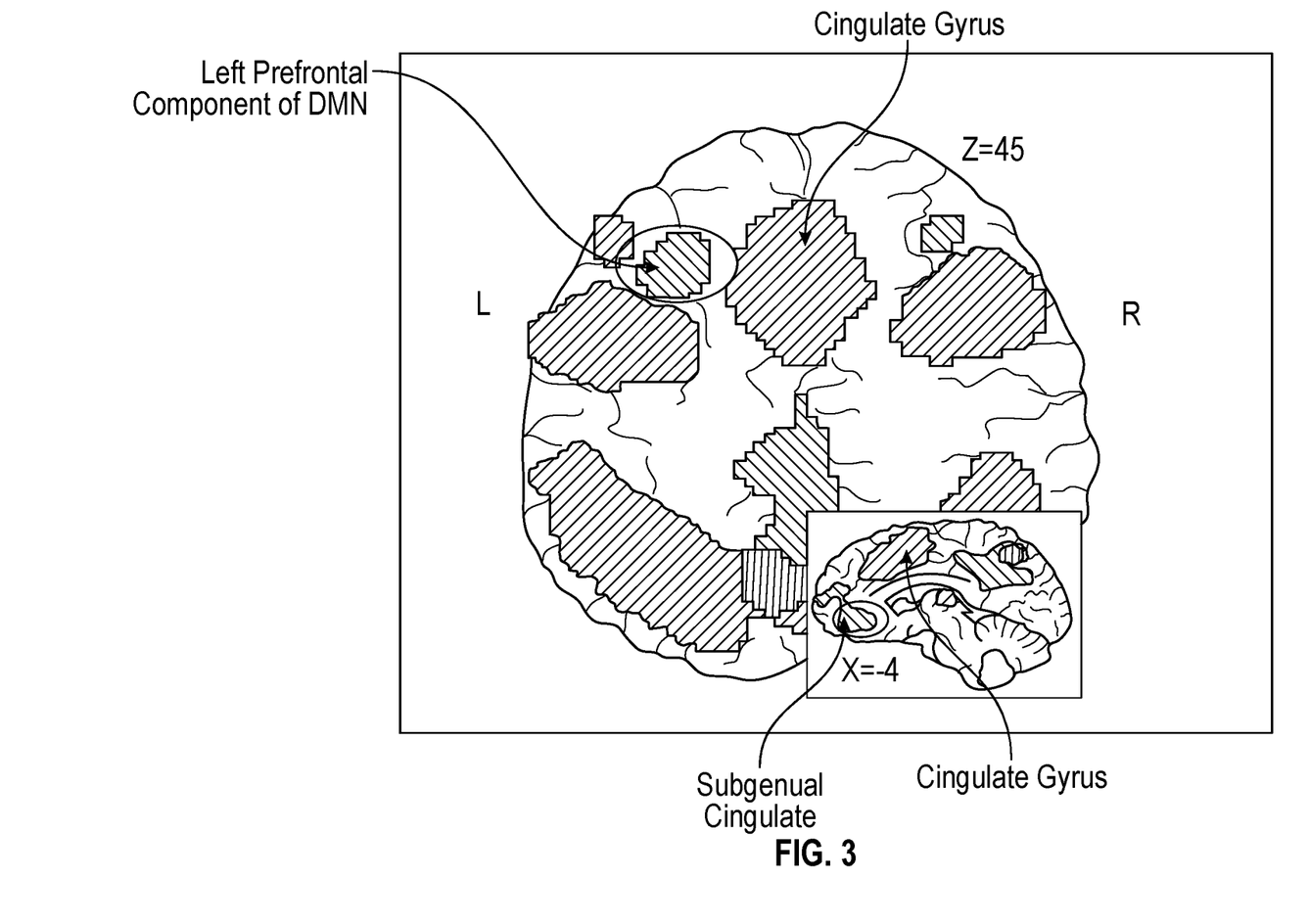
FIG. 3 is a diagram of a connectivity-based parcellation of dorsolateral prefrontal cortex showing anterior zone connecting strongly to sub-genual cingulate in accordance with an embodiment of the present invention.

With a "downstream aiming" method, stimulating anterior DLPFC produces changes in connectivity in the subgenual cingulate gyrus, based on connectivity-based parcellation (CBP) of the DLPFC into two zones with distinct connectivity as shown in FIG. 3, which is a diagram of a connectivity-based parcellation of dorsolateral prefrontal cortex showing anterior zone connecting strongly to subgenual cingulate. Note that this model is based on meta-analysis of the BrainMap database.

The rationale for selecting the subgenual cingulate as a target was based on its position within the limbic system and implication in psychiatric symptoms, including post-traumatic stress disorder (PTSD).

In a trial of irTMS in PTSD, a treatment plan was based on resting-state fMRI obtained in each subject before treatment. The plan was determined based on the connectivity between anterior DLPFC and subgenual cingulate, selecting a stimulation location in anterior DLPFC that was strongly connected to subgenual cingulate. Once this zone was identified, the C3 aiming principle was applied to create a treatment target. Patients were randomized to active TMS or sham TMS, using a two-sided, unmarked coil. Neither the patient nor the treatment technician was aware of whether the active or sham treatment was being delivered.

The trial began in July 2017. As of Sep. 24, 2018, 95 participants have begun treatment; 91 have completed ≥10 treatments; and, 86 have completed ≥15 treatments. Of those completing ≥10 treatments, 88 have completed post-treatment MRI.

Figure 4:
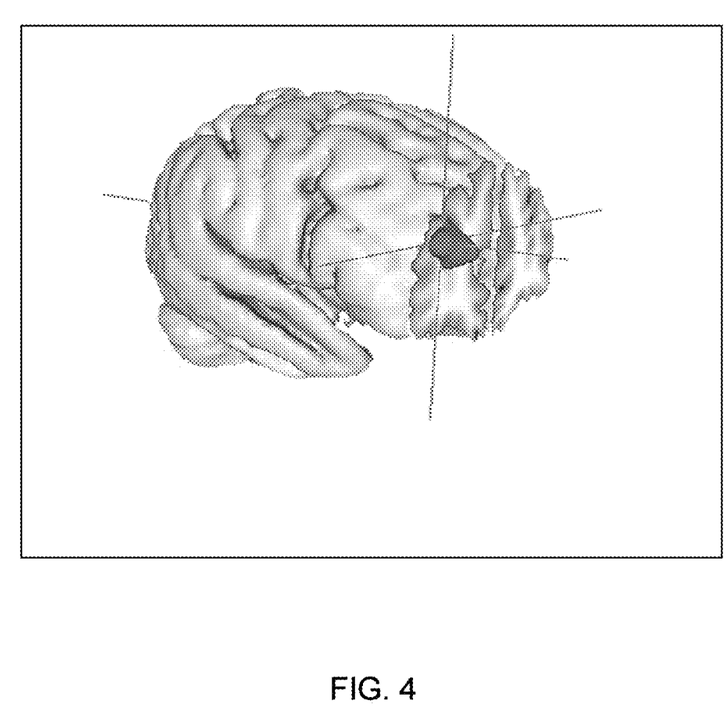
FIG. 4 is an illustration of a seed region in anterior dorsolateral prefrontal cortex.

From the group that had completed ≥10 treatments AND had had post-treatment MRI, 25 from each group (active and sham) were selected at random. A Group×Time interaction statistical analysis was performed to identify the brain voxels showing the greatest pre/post change in functional connectivity with the anterior DLPFC (the targeted zone) as a function of group membership. The analysis was performed in a "seed-to-whole-brain" manner, using the anterior DLPFC as the seed region as shown in FIG. 4, but assessing responses in a voxel-wise, whole-brain manner. In FIG. 4, a seed region in anterior DLPFC is shown, defined in 3D standardized coordinates as an irregular region fit to the average anterior DLPFC, per the connectivity-based parcellation analysis.

Figure 5:
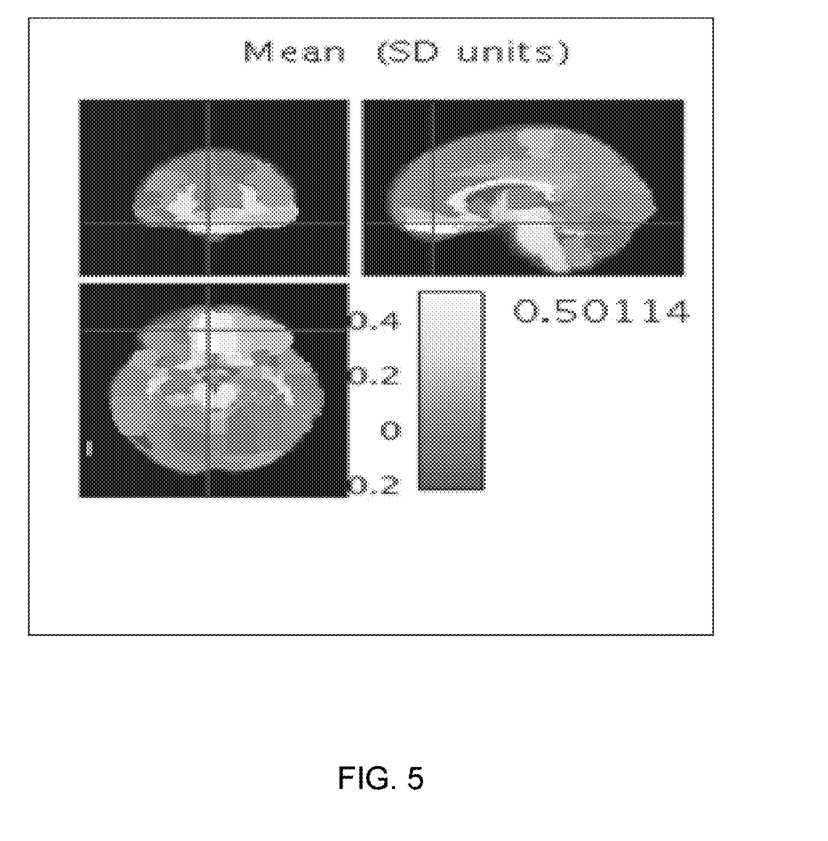
FIG. 5 is a block diagram of a Group×Time analysis in accordance with an embodiment of the present invention.

The result of the Group×Time interaction analysis strongly confirmed the efficacy of "downstream aiming" method. The greatest pre- to post-treatment change in functional connectivity was in the subgenual cingulate gyrus, the intended "downstream" target as shown in FIG. 5 which is a block diagram of a Group×Time analysis. As shown, the greatest pre-to-post treatment change in functional connectivity was in the esubgenual cingulate gyrus, the intended downstream target. Note that units are in standard deviation (effect size) units, showing a neurobiological moderate treatment effect.

Following is a more detailed narrative of the trial.

A randomized, double-blind, sham-controlled, 4-week trial of TMS was performed to the right (or left) dorsolateral prefrontal cortex (DLPFC) for active duty military with post-traumatic stress disorder (PTSD) who were concurrently receiving trauma-focused psychotherapy (i.e., Prolonged Exposure (PE) or Cognitive Processing Therapy (CPT)) as a standard of care along with standard pharmacological management at LRTC.

Arm 1 delivers active irTMS to the right DLPFC. Arm 2 delivers active irTMS to the left DLPFC. Arm 3 delivers sham TMS (inactive coil) to DLPFC (counter-balanced between the right and left DLPFC sites).

In all three arms, the following stimulation protocol was used: 20 Hz rTMS (active or sham) delivered in 2 sec trains with 28 sec inter-train intervals, 20 minutes/session (i.e. 1,600 pulses/session), 5 sessions/week, for 4 weeks. In arm 3, sham TMS uses a TMS coil that simulates the appearance, sound, and scalp stimulation of TMS but does not deliver an electric field (E-field) to the brain. All three arms include comparable and repetitive image-guided, robotic movements of the TMS coils to ensure both therapist blinding and equivalent placebo effects across arms. Neuroimaging was used both for treatment planning and to characterize any treatment-related network plasticity using resting-state fMRIs (rs-fMRIs) at baseline, and after 2 and 4 weeks of treatment in each arm. CAP common-data elements to self-report PTSD and depressive symptoms (i.e., PCL and PHQ-9) and neuropsychological tests was administered at baseline and weekly throughout treatment (weeks 1-4). Clinical assessments of PTSD and depression using the CAPS-5 and MADRS was completed before and after treatment. Finally, a 3-month follow-up was conducted over the phone to evaluate maintenance of all clinical outcomes.

Aims and Hypotheses

Aim 1. Test for irTMS-induced improvements in symptoms in active duty military with combat-related PTSD.

Hypothesis 1a. irTMS to the right DLPFC will be superior to sham TMS in relieving PTSD symptoms.

Hypothesis 1b. irTMS to the left DLPFC will be superior to sham TMS in relieving depressive symptoms in PTSD patients with comorbid MDD.

Aim 2. Test for irTMS-induced changes in network functionality using rs-fMRI.

Hypothesis 2a. Intrinsic connectivity will be attenuated by active irTMS in networks connected to the respective treatment sites, as tested by correlation with the number of sessions received at the time of scanning and by pre-treatment vs. post-treatment contrast.

Hypothesis 2b. Treatment-induced decreases in connectivity will correlate with symptom improvement within and across treatment arms.

Connectivity-based parcellation of the DLPFC was performed using meta-analytic connectivity-mapping methods. The DLPFC was seeded in the BrainMap database to identify local projections from the DLPFC to surrounding regions using MACM. This produced a large (721 2×2×2 mm voxels), contiguous region of interest including the left superior and middle frontal gyri. This volume of interest was divided into sub-regions using connectivity-based parcellation as shown in FIG. 6, conjointly applied to the BrainMap database and to a large resting-state fMRI dataset.

Figure 6:
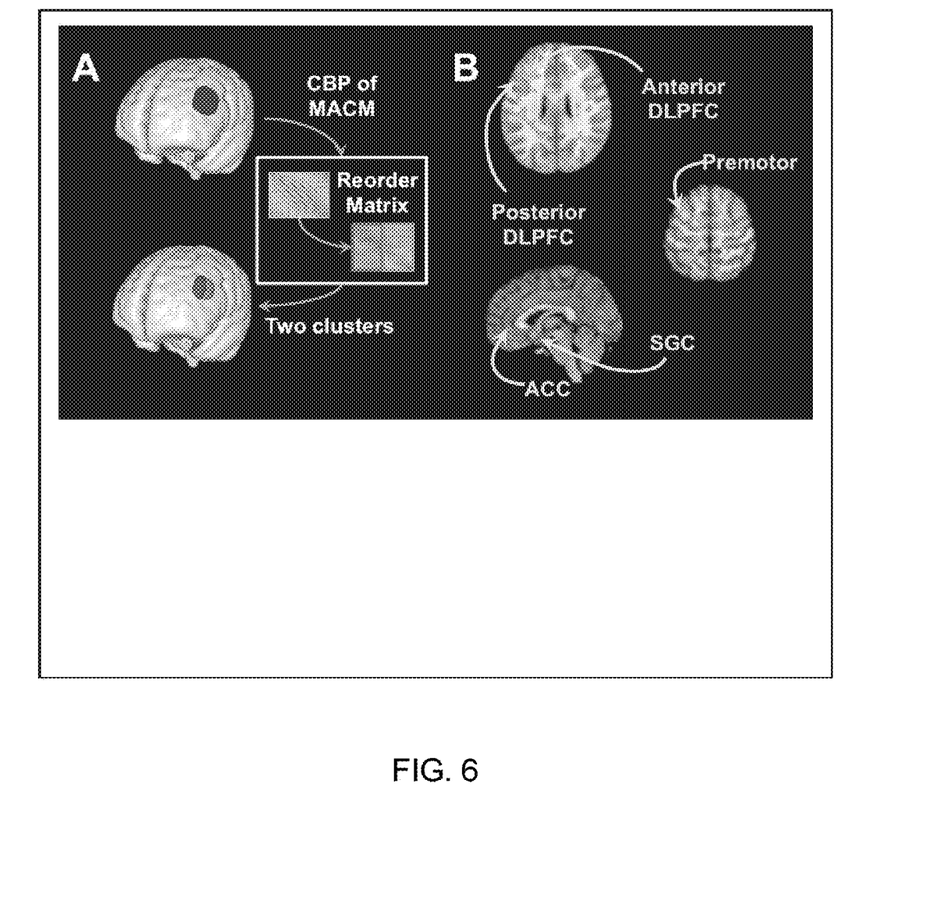
FIG. 6 is an illustration of connectivity based parcellation examples.

In FIG. 6, connectivity based parcellation (CBP) of the meta-analytic connectivity models (MACM) of the dorsolateral prefrontal cortex (DLPFC) produces two separate sub-regions: the anterior (DLPFC-limbic; red) and the posterior (DLPFC-premotor; green). Each seed region produces a group-wise functional connectivity map for each cluster. In this study, regions connected to the subgenual cingulate (SGC) and/or the anterior cingulate cortex (ACC) will be used for subject-specific left or right DLPFC targets.

In a conjunction analysis, two discrete clusters were observed as shown in FIG. 6, each characterized by different projection patterns. These were: 1) a DLPFC-Limbic pathway (red, FIG. 6), projecting to the SGC (BA 25) and the ACC (BA 24); 2) a DLPFC-Premotor pathway (green, FIG. 6). Therefore, the working hypothesis is that to improve rTMS-induced treatment outcomes in PTSD, a network-specific targeting of PTSD must be achieved. To the inventors' knowledge, this is the first application of connectivity-based parcellation for rTMS targeting.

The irTMS treatments in this trial target the DLPFC, a brain region strongly implicated as a hub in brain networks dysregulated in PTSD and depression. Specifically, PTSD patients show a hypo-activation of the prefrontal cortex, with both increases and decreases demonstrated throughout connected brain regions. A recent meta-analysis of PTSD neuroimaging studies identified the anterior cingulate cortex (ACC) and the posterior cingulate cortex (PCC) as the primary hubs in PTSD networks. PTSD severity was associated with higher metabolism in the precuneus and the dorsal ACC. Further analysis has shown that PTSD patients demonstrated increases in effective connectivity between the left DLPFC and: 1) the precuneus and 2) the PCC—with both pathways returning to normal connectivity strengths after cognitive behavioral therapy. The PCC, precuneus, and ACC are too far from the scalp to be viable targets for rTMS, however, the DLPFC has been the target of the vast majority of TMS treatment trials in PTSD, depression, and other disorders. Furthermore, the effects of PTSD appear to be lateralized, demonstrating hypo-activation of the right prefrontal cortex whereas MDD exhibits hypo-activation on the left prefrontal cortex.

Since high-frequency rTMS has been shown to increase local cerebral blood flow, high-frequency (20 Hz) rTMS may be delivered at each DLPFC treatment site (in respective arms) to maximally drive targeted prefrontal cortices. Thus, our primary hypothesis (1a) is that right DLPFC irTMS will relieve PTSD symptoms, whereas our secondary hypothesis (1b) is that left DLPFC irTMS will relieve depressive symptoms in PTSD patients with comorbid MDD. In addition, since the right DLPFC is thought to inhibit its left homologue, we believe that the increased effective connectivity observed in PTSD patients (e.g. left DLPFC←←PCC) will also be inhibited, thereby decreasing PTSD symptoms. The acquisition of rs-fMIRIs throughout the study will validate these hypotheses and may yield valuable information on the mechanism(s) of PTSD.

DLPFC is a large, functionally heterogeneous region with an anterior-to-posterior functional gradient. Here we propose to target the right and left DLPFC locations with the strongest projections to SGC and ACC, as determined by per-subject resting-state fMRI. The concept of connectivity-based, image-guided TMS delivery has been proposed but no treatment trials using this per-subject intrinsic connectivity (or cortical surface geometry) approach have been reported. Here we propose to apply this individually optimized treatment strategy.

All participants will be imaged using a research-dedicated 3T Siemens TIM/Trio MRI scanner (Siemens, Erlangen, Germany) with an eight-channel phased array coil, using the recently proposed CAP common data elements for neuroimaging—which consist of 1) high-resolution T1 and T2-weighted structural images, 2) diffusion tensor imaging (DTI), and 3) resting-state blood oxygen dependent (BOLD) fMRI. Structural imaging will be obtained only once, upon enrollment. Structural images will be used for rTMS treatment planning and for spatial normalization to a standard anatomical template. Functional images will be obtained up to three times (e.g. initial MRI session, mid-treatment, post-treatment) across the course of the study and used to detect symptom-specific abnormalities and treatment-induced physiological adaptations. Each patient will wear foam earplugs during each image acquisition and rTMS treatment session to protect patients from the high decibel level produced by the MRI gradient and rTMS pulses. PTSD and MDD symptom assessments will be obtained weekly, immediately following each fMRI and/or rTMS treatment session at the designated assessment interval. All imaging data will be pre-processed and analyzed.

T1- and T2-weighted structural MRIs will be used for treatment-plan computation (described above) and for spatial normalization of functional images. T1-weighted images are obtained in 3D modes (0.8 mm cubic voxels) with acquisition parameters of: TR=2300 ms, TE=2.86 ms, tip angle=9°, slice thickness=0.8 mm, in-plane resolution=0.8× 0.8 mm$^2$ acquiring 160 volumes. T2-weighted images will be obtained with and without fat suppression (turbo spin echo, 96 sagittal slices, matrix size=256×256, voxel size=1× 1×2 mm$^3$, flip angle=110°, TR/TE=11990/102 ms, turbo factor 11). Each acquisition will be repeated three times to increase signal-to-noise. Total structural MRI scan time is approximately 32 minutes. To ensure accurate E-field modeling, we will also acquire DTI. DTI will be obtained from the diffusion-weighted images using a single-shot echo-planar gradient-recalled echo, T2-weighted, sequence to acquire diffusion-weighted data with the spatial resolution of 1.5×1.5×3.0 mm and TE/TR=87/8000. The diffusion-weighted scans will have 32 different non-collinear diffusion sensitization directions, consisting of diffusion-weighted images at b=700 mm2/s and one non-diffusion weighted image at b=0 mm$^2$/s. The total DTI sequence acquisition time will be 12 min.

The T1- and T2-weighted images will be pre-processed using FSL's Brain Extraction Tool, then segmented into three tissue classes: gray, white and ventricular components, using the FMRIB's Automated Segmentation Tool. Acquisition of both the T1- and T2-weighted images allow more accurate tissue segmentation and TMS treatment planning; the gray-matter surface normal will be used for treatment planning. Images will be spatially normalized to Montreal Neurological Institute space for group-wise analyses. The DTI data will be pre-processed using FSL's diffusion toolbox.

Intrinsic connectivity networks will be measured using blood oxygen dependent (BOLD) fMRI. BOLD fMRI is the most robust and widely used pulse sequence for intrinsic connectivity modeling. BOLD images will be used for computing treatment plans and for testing for intrinsic connectivity changes by symptom score and with treatment. BOLD data will be acquired as 300 whole-brain volumes acquired with a TR=3000 ms, TE=30 ms, tip angle=90°, 128×128 voxels, 2 mm×2 mm, and 49 slices (2.6 mm thickness). This sequence requires ~15 minutes. Data will be analyzed using FSL's FEAT program. Head movements will be corrected by affine registration using a 2-pass procedure. BOLD data will be normalized to MNI space single-subject template using the "unified segmentation" approach, followed by a 5-mm full width at half maximum Gaussian smoothing. Spurious correlations with nuisance variables are removed using a recently validated framework. Data are band-pass filtered preserving frequencies between 0.01 and 0.08 Hz. The time course of each seed region's BOLD signal will be extracted as the first eigen-variate of activity in all gray-matter voxels located within the respective cluster. To quantify resting-state functional connectivity linear correlation coefficients between the time series of the seeds (i.e., targeted DLPFC nodes of each subject's network) and any other gray matter voxel will be computed. Voxel-wise correlation coefficients will be transformed into Fisher's Z-scores (with non-sphericity correction) prior to symptom- and and pathway-correlation analyses.

Functional images were also used to identify each subject's primary motor cortex for motor threshold assessment. BOLD fMRI will be acquired in a block design paradigm utilizing gradient echo planar images with the following parameters: TR=2 s, TE=45 ms, a flip angle of 90°, and slice thickness=6 mm. Twenty continuous slices will be acquired, with an in-plane spatial resolution of $3\times3$ mm$^2$. During the BOLD fMRI scan, participants will perform abduction and adduction of the right index finger (in a block design); this has been shown to maximally activate the first dorsal interosseous muscle area of the hand's motor cortex. The task and rest periods are 30 seconds long and are interleaved during the 6 minutes of data acquisition. During the rest period, the participants will be instructed to remain motionless, to keep their eyes open, and to perform no behavioral task. Each patient's BOLD fMRI will be analyzed using FSL's FEAT to determine his/her primary motor cortex targets for motor threshold assessment.

Figure 7:
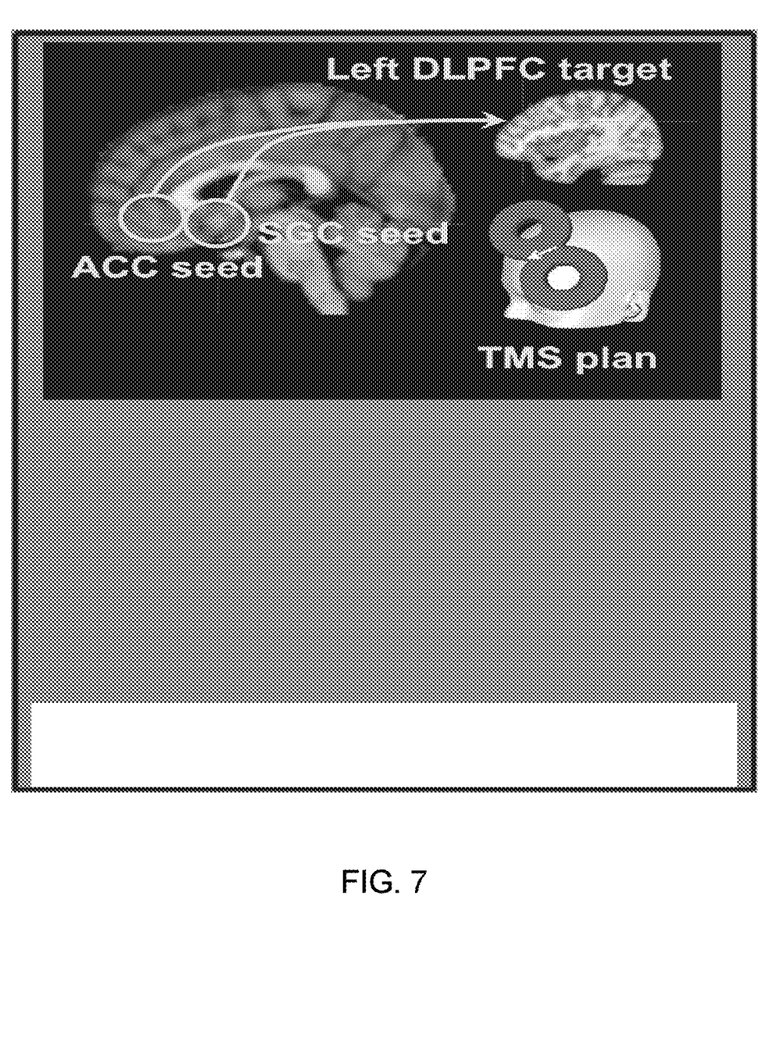
FIG. 7 is a block diagram of connectivity-based DLPFC treatment planning in accordance with an embodiment of the present invention.

All rTMS treatments will be planned and delivered using a robotic, image-guided system. MRI images will be acquired and used to compute subject-specific, treatment plans as shown in FIG. 7, which is a block diagram of connectivity-based DLPFC treatment planning in accordance with an embodiment. Such treatment plan is stored and used during a given subject's respective rTMS treatment sessions. The seed region for resting-state connectivity analysis will be the subgenual cingulate (SGC) and/or the anterior cingulate cortex (ACC) as defined by the connectivity-based parcellation of the DLPFC. This seed will be used to identify a target zone within each subject's DLPFC to produce a subject-specific rTMS treatment plan. TMS coil position & orientation will be optimized for maximal effective E-field in each subject/target. Note that both approaches require specific TMS coil orientations. The arrow in FIG. 7 represents the direction of the induced E-field.

Image guidance will be based on treatment plans developed from high-resolution structural MRI and resting-state BOLD fMRI. Anatomical images are acquired as high-resolution (0.8 mm$^3$), 3-D T1-weighted images on a 3T Siemens TIM/TRIO. From the T1 MRI, two surface models are computed: a model of the scalp surface, for use in registration of the subject to the treatment plan; and, a model of the cortical surface including cortical surface normals. Both models are created using a modification of the dividing cubes algorithm following automated tissue segmentation. The scalp surface model is based on the air-scalp interface, which is readily obtained by simple thresholding. The cortical surface is based on pre-classification of brain tissue into gray, white and CSF surfaces, using the FMRIB's Automated Segmentation Tool.

Each subject's primary motor cortex (determined using BOLD fMRI; described above) will be used as a target for motor threshold assessment. The coil-to-cortex depth required for motor threshold-level E-field strengths will be calculated using methods/models. These subject-specific E-field models will inform depth-corrected E-field strengths in other coil poses. In each treatment group, either active or sham rTMS will be delivered to the DLPFC regions projecting either into the left DLPFC (Arm 1) or the right DLPFC (Arm 2); the sham group will be equally divided into left and right treatment sites (Arm 3). For each subject, candidate locations will be identified by region-seeded analysis of their resting-state BOLD fMRI. For each group, the seed region will be in the subgenual cingulate cortex (SGC; BA 25) and/or the anterior cingulate cortex (ACC; BA 24) as defined by the connectivity-based parcellation of the DLPFC and determination of the cluster-based connectivity described above. For either pose/pathway, a coil location/orientation will be computed to provide the maximal effective E-field (i.e., column-aligned, depth-corrected E-field) within the target zone of the DLPFC. An example treatment plan is shown in FIG. 7.

An image-guided treatment plan will be computed for sham TMS subjects in the same manner as for active irTMS to ensure therapist blinding.

For each subject, the coil pose will be pre-computed from structural and functional MRI and stored as an individualized treatment plan. Each subject's treatment plan will be registered to his/her head by creating a scalp model with a high-resolution digitizer, an integrated component of the irTMS system. In each arm, the TMS coil will be positioned and held by the robot (under therapist supervision) to ensure accurate and reproducible coil positioning throughout and between rTMS treatment sessions.

rTMS will be performed as follows. Participants recline supinely on a foam-padded, custom-built treatment table, which is mounted with a padded headrest and velcro-strap head-restraint system. Once the head is stabilized, the scalp surface is mechanically digitized, creating a 3D in situ scalp model. The in situ scalp model is registered to the MRI-derived scalp model stored in the treatment plan using the convex-hull algorithm. Once patient and model are registered, the TMS coil is positioned according to the previously computed treatment plan. TMS set-up requires ~10 minutes.

To determine each patient's motor threshold, we will position the TMS coil at each subject's prescribed motor TMS treatment plan. Once contact and position have been established, the patient will be instructed to extend their right index finger. The intensity of the TMS coil will be increased (in steps of 10%) from 20% to 100% machine output. The intensity at which TMS produces a motor evoked potential greater than 100 µV on more than five out of ten electromyographic (EMG) trials will be recorded. The EMG recordings for this procedure will use a Synamp Evoked Response Potential recording system recording form the first dorsal interosseous muscle. We will adjust the TMS intensity to ±10% of the initial motor threshold in steps of 2% machine output. The TMS coil's position and intensity will be used for E-field calculation of the depth-corrected E-field strengths for each subject's DLPFC target.

At the respective TMS treatment target site, active rTMS treatments will be delivered to the left DLPFC (n=50) or right DLPFC (n=50) using a TMS treatment protocol of 2 seconds of 20 Hz rTMS followed by a 28 second rest period; the treatment lasts for a total of 20 minutes (e.g. 1,600 rTMS pulses). The rTMS protocols will be delivered with a liquid cooled figure-8 MagPro (MagVenture, Denmark) coil at a depth-corrected TMS intensity of 100 Volts/meter. Each patient's motor threshold will be determined prior to the first TMS session and their depth-corrected E-field will be calculated to gauge the accurate dosage of 100 V/m at the treatment target site. rTMS treatments will be delivered 5 days per week (Mon-Fri) during the four treatment weeks. In arm 3 (n=50), sham TMS uses a TMS coil that simulates the appearance, sound, and scalp stimulation of TMS but does not deliver an electric field (E-field) to the brain.

Initial diagnosis and weekly symptom assessment will be performed by the clinical assessment team who will be blinded to the subjects' treatment arm. PTSD diagnosis as part of the initial screening will be based on the CAPS-5, a structured interviewer administered instrument, which corresponds to DSM criteria for PTSD. The CAPS will be used in conjunction with the Life Events Checklist (LEC) to make a current (past month) or lifetime diagnosis of PTSD or to assess symptoms over the past week. Given the large number of ratings and their compression over time, the gold-standard measurement for PTSD (CAPS) would be overly burdensome to the study subjects and affect their programming at LRTC therefore weekly symptoms will be assessed using a self-report the PCL-5 while the CAPS-5 only will be completed at baseline, end of treatment (week 4) and 3 mo post-treatment. Clinical Global Impressions (CGI) will be used following the procedures of the STRONGSTAR trials. The Outcome Questionnaire-45 (OQ-45) will be used to estimate subjects baseline overall disease severity and overall measure of the outcomes of treatment. The Emotional Regulation Questionnaire (ERQ) will be used measure treatment induced changes of both cognitive reappraisal and expressive suppression of emotions. To evaluate mood symptomatology we will use the Montgomery-Asberg Depression Rating Scale (MADRS), the clinician rated Bipolar Inventory of Symptoms Scale (BISS-15) and the BISS Self Report (BISS-SR), and the Quick Inventory of Depressive Symptoms—Self-Report (QIDS-SR). Treatment side effects will be captured using the Systematic Assessment for Treatment Emergent Effects (SAFTEE). We will also obtain an assessment of sleep, the Pittsburg Sleep Quality Index (PSQI), which has been amended for PTSD-related sleep problems. Suicidal ideation will be assessed at baseline via the Columbia Suicide Severity Rating Scale (CSSRS). Weekly, the Beck Scale for Suicide Ideation (BSSI) will be utilized for ongoing assessment of suicidal ideation. The World Health Organization Disability Schedule (WHODAS) will be used to capture functional outcome measures. The three-month clinical follow up after treatment completion will be conducted over the phone.

A brief computerized neuropsychological test battery that shows no practice effects and is suitable for clinical trials, will be used to examine the cognitive effects of the treatment. The proposed blood collection and banking, is consistent with our goals of investigating biomarkers of response and treatment trajectories, initially focusing on plasma levels of selected inflammatory mediators and will also permit future hypothesis driven analyses to interrogate the mechanisms underlying the effects of TMS on PTSD symptoms. Neurocognitive testing and blood collection will be conducted at baseline and treatment week 2 and 4.

Effect size estimation for irTMS was based on the most relevant prior PTSD/TMS. In earlier PTSD/TMS trials, 10 Hz rTMS of the right DLPFC was compared to sham and obtained a large effect size of 1.84. 20 Hz rTMS of the right DLPFC was compared to sham and obtained a very large effect size of 3.78. In addition, MDD/TMS trials have compared image-guided TMS to socTMS of the left DLPFC (no sham) and obtained an effect size of 0.4. The technical advances of this irTMS approach over earlier trials, as well as the longer treatment duration described herein, would predict an even greater effect size. Nevertheless, we conservatively estimate the effect size of irTMS at 1.00. To obtain power=0.80, 17 completing subjects per arm will be required. In view of the drop-out rates of the multi-site MDD/TMS trials, we propose to enroll 50 subjects per active treatment arm, anticipating at most a 33% drop-out rate (i.e. at least 33 patients per group); this will give us a power=0.98.

Figure 8:
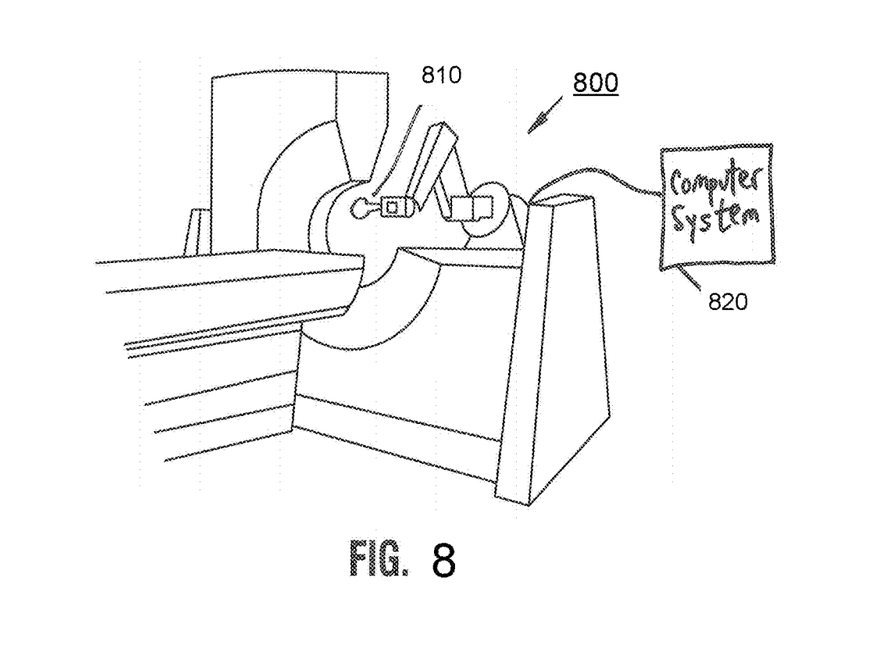
FIG. 8 is a block diagram of a system in accordance with one embodiment of the present invention.

Embodiments can be implemented, in part, by instructions to be executed by at least one computer system and stored on at least one non-transitory storage medium. To this end, one or more computers each with a processor and one or more storages may include instructions to perform the described methods for receiving subject image data and generating a TMS treatment plan, and for delivering the TMS robotically to the subject. In addition, one or more additional computer systems may be used to obtain training set data, develop a machine learning model, and use the model to generate a treatment plan based on an individual subject's imaging data. FIG. 8 is a block diagram of a system in accordance with one embodiment of the present invention. As shown in FIG. 8, a robot 800, which may have six degrees of freedom, has a TMS coil 810 attached to a distal end may be controlled as described herein using a computer 820 that executes one or more sets of instructions stored in a storage of the computer to realize the TMS operations described herein.

Figure 9:
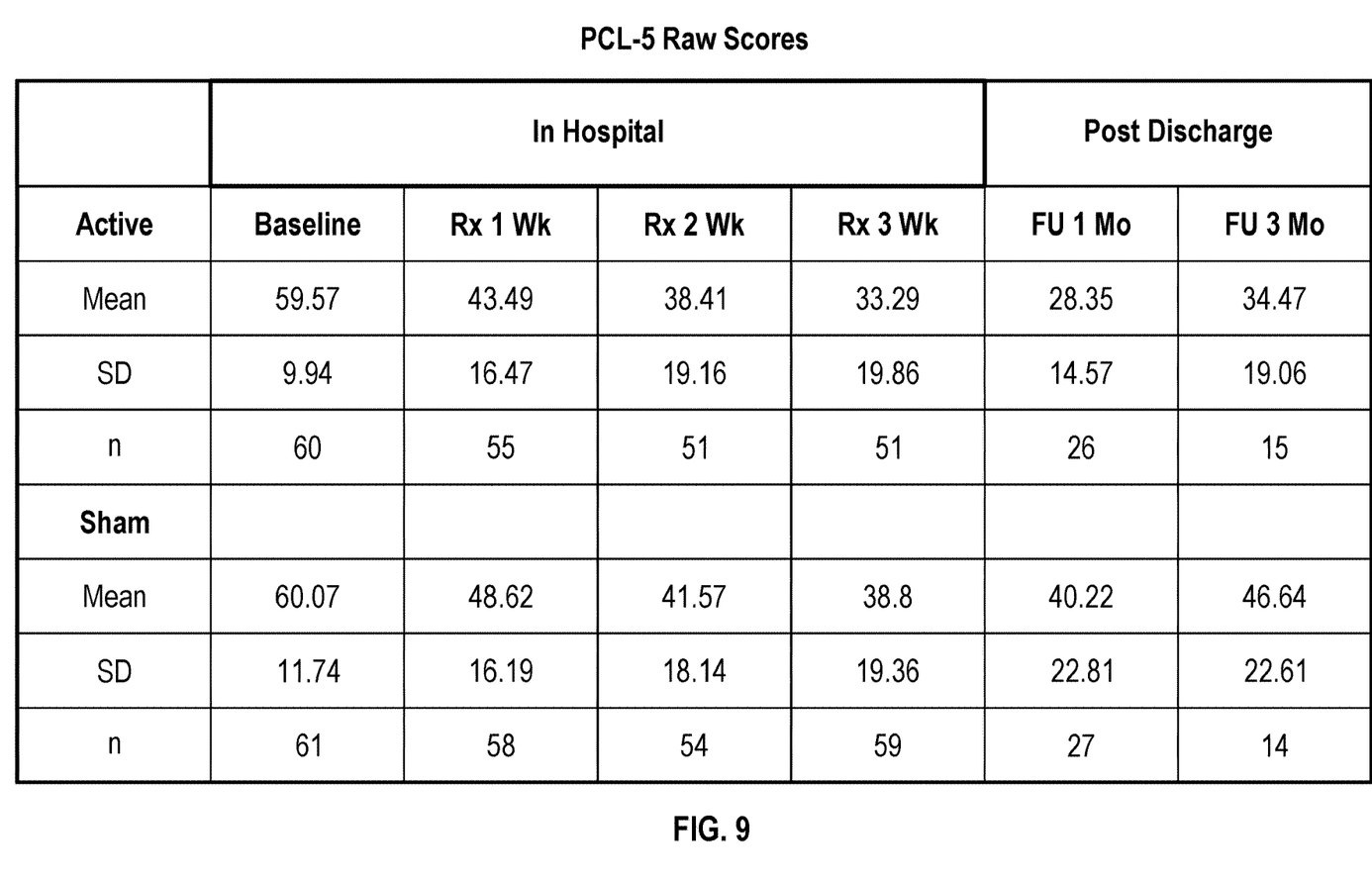
FIG. 9 is a tabular illustration of PCL-5 raw scores for trial participants in an example trial using an embodiment.
Figure 10:
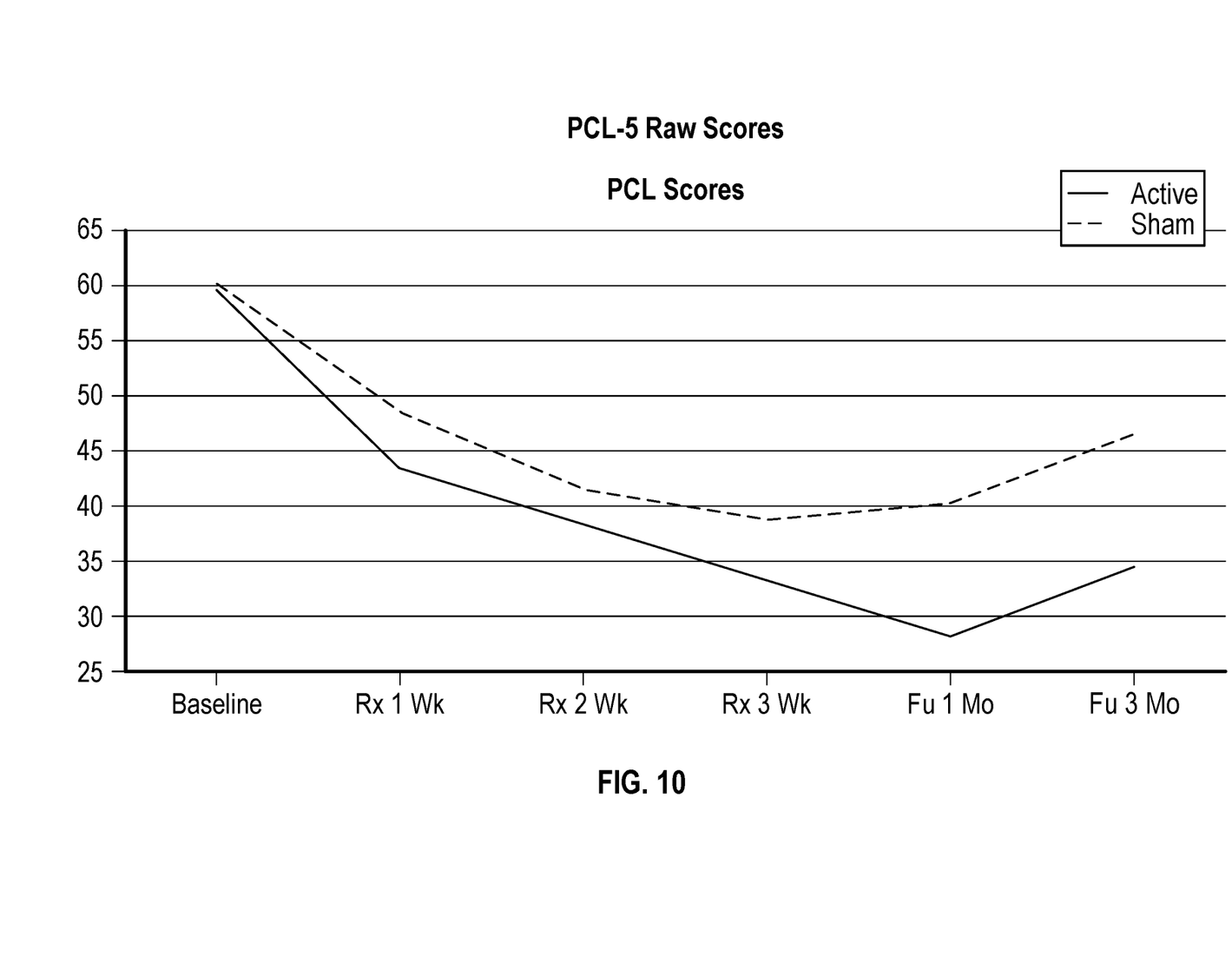
FIG. 10 is a graphical illustration of PCL-5 raw scores for trial participants in an example trial using an embodiment.
Figure 11:
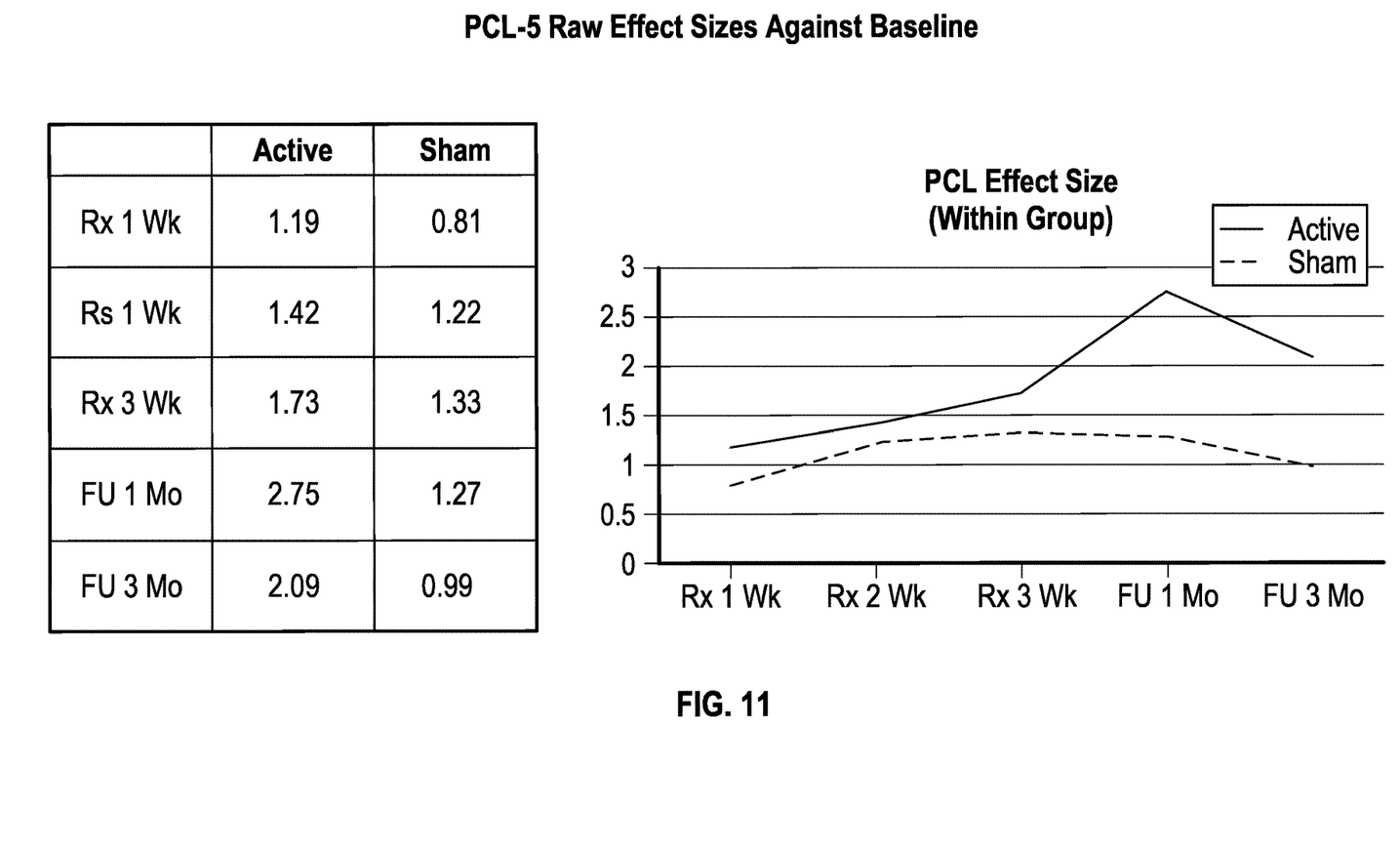
FIG. 11 is a tabular illustration of PCL-5 raw effect sizes for trial participants in an example trial using an embodiment.

FIGS. 9-11 show results of the above-described trial performed using an embodiment. In FIG. 9 a tabular illustration of PCL-5 raw scores for trial participants in the example trial is shown. In FIG. 10 a graphical illustration of PCL-5 raw scores for trial participants in the example trial is shown. In FIG. 11 a tabular illustration of PCL-5 raw effect sizes for trial participants in the example trial is shown.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:
1. A method for delivery of transcranial magnetic stimulation (TMS) to a subject, comprising:
   identifying, based at least in part on a connectivity-based parcellation, a first upstream target brain region;
   computing, in at least one computing system, a region-seeded connectivity map of the first upstream target brain region of the subject based at least in part on a brain network connectivity;
   identifying at least one downstream projection region of the subject associated with the first upstream target brain region of the subject, wherein the first upstream target brain region comprises anterior dorsolateral prefrontal cortex and the at least one downstream projection region comprises subgenual cingulate;
   computing, in the at least one computing system, a region-seeded connectivity map of the at least one downstream projection region of the subject;
   identifying a first upstream projection region of the subject that demonstrates functional connectivity to the at least one downstream projection region of the subject;
   determining positioning for a TMS coil with respect to the first upstream projection region of the subject in accordance with a cortical column cosine aiming principle; and causing delivery of the TMS to the subject via the TMS coil according to the determined positioning.

2. The method of claim 1, further comprising treating the subject for post-traumatic stress disorder via the TMS delivery.

3. The method of claim 1, further comprising treating the subject for depression via the TMS delivery.

4. The method of claim 1, further comprising applying the connectivity-based parcellation to task-activation data to identify one or more sub-zones within the at least one downstream projection region based on remote co-activation patterns.

5. The method of claim 1, further comprising computing the region-seeded connectivity map using functional magnetic resonance imaging data of the subject.

6. The method of claim 5, further comprising determining the TMS coil positioning in accordance with the cortical column cosine aiming principle using the functional magnetic resonance imaging data and structural magnetic resonance imaging data of the subject.

7. The method of claim 5, wherein the region-seeded connectivity map comprises a subject-specific functional connectivity mapping of the at least one downstream projection region.

8. The method of claim 1, further comprising causing the TMS delivery via a robotic member having at least six degrees of freedom.

9. The method of claim 1, further comprising:
obtaining a training set having a plurality of entries, each of the plurality of entries associating image data of a person with a treatment plan for the person; and
developing a model based on the training set.

10. The method of claim 9, further comprising:
receiving image data of the subject; and
generating, via the model, a treatment plan for the TMS delivery to the subject using the image data of the subject.

11. A system for transcranial magnetic stimulation (TMS) comprising:
a robotic member having a distal portion and a proximal portion, the robotic member having at least six degrees of freedom;
a coil for generating an electric field, the coil coupled to the distal portion of the robotic member; and
at least one computing system to execute instructions stored in a non-transitory storage medium, the instructions to cause the at least one computing system to:
identify, based at least in part on a connectivity-based parcellation, a first upstream target brain region of a subject;
compute a region-seeded connectivity map of the first upstream target brain region of the subject based at least in part on a brain network connectivity;
identify at least one downstream projection region of the subject associated with the first upstream target brain region of the subject, the first upstream target brain region comprising anterior dorsolateral prefrontal cortex and the at least one downstream projection region comprising subgenual cingulate;
compute a region-seeded connectivity map of the at least one downstream projection region of the subject;
identify a first upstream projection region of the subject that demonstrates functional connectivity to the at least one downstream projection region of the subject;
determine positioning for the coil with respect to the first upstream projection region of the subject in accordance with a cortical column cosine aiming principle; and
cause delivery of the TMS to the subject via the coil according to the determined positioning.

12. The system of claim 11, wherein the instructions further cause the at least one computing system to treat the subject for post-traumatic stress disorder via the TMS delivery.

13. The system of claim 11, wherein the instructions further cause the at least one computing system to treat the subject for depression via the TMS delivery.

14. The system of claim 11, wherein the instructions further cause the at least one computing system to compute the region-seeded connectivity map using functional magnetic resonance imaging data of the subject.

15. The system of claim 14, wherein the instructions further cause the at least one computing system to determine the TMS coil positioning in accordance with the cortical column cosine aiming principle using the functional magnetic resonance imaging data and structural magnetic resonance imaging data of the subject.

16. A non-transitory computer readable medium comprising instructions, that when executed, cause a computing system to:
identify, based at least in part on a connectivity-based parcellation, a first upstream target brain region of a subject;
compute a region-seeded connectivity map of the first upstream target brain region of the subject based at least in part on a brain network connectivity;
identify at least one downstream projection region of the subject associated with the first upstream target brain region of the subject, the first upstream target brain region comprising anterior dorsolateral prefrontal cortex and the at least one downstream projection region comprising subgenual cingulate;
compute a region-seeded connectivity map of the at least one downstream projection region of the subject;
identify a first upstream projection region of the subject that demonstrates functional connectivity to the at least one downstream projection region of the subject;
determine positioning for a TMS coil with respect to the first upstream projection region of the subject in accordance with a cortical column cosine aiming principle; and
cause delivery of the TMS to the subject via the TMS coil according to the determined positioning.

17. The non-transitory computer readable medium of claim 16, further comprising instructions, that when executed, cause the computing system to treat the subject for one or more of depression and post-traumatic stress disorder via the TMS delivery.

18. The non-transitory computer readable medium of claim 16, further comprising instructions, that when executed, cause the computing system to compute the region-seeded connectivity map using functional magnetic resonance imaging data of the subject.

19. The non-transitory computer readable medium of claim 18, further comprising instructions, that when executed, cause the computing system to determine the TMS coil positioning in accordance with the cortical column cosine aiming principle using the functional magnetic resonance imaging data and structural magnetic resonance imaging data of the subject.

* * * * *